(12) United States Patent
Okazaki et al.

(10) Patent No.: US 8,519,185 B2
(45) Date of Patent: Aug. 27, 2013

(54) PROCESS FOR PRODUCING GLYCOLIC ACID

(75) Inventors: Shinya Okazaki, Ichihara (JP); Kaori Matoishi, Ichihara (JP); Kiyoshi Itou, Tokyo (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 1246 days.

(21) Appl. No.: 12/084,118

(22) PCT Filed: Oct. 26, 2006

(86) PCT No.: PCT/JP2006/321389
§ 371 (c)(1),
(2), (4) Date: Apr. 25, 2008

(87) PCT Pub. No.: WO2007/049707
PCT Pub. Date: May 3, 2007

(65) Prior Publication Data
US 2010/0022740 A1    Jan. 28, 2010

(30) Foreign Application Priority Data
Oct. 26, 2005   (JP) ................................. 2005-311323

(51) Int. Cl.
*C07C 51/42*    (2006.01)
(52) U.S. Cl.
USPC ............ 562/580; 562/512; 562/579; 562/589
(58) Field of Classification Search
None
See application file for complete search history.

(56) References Cited

U.S. PATENT DOCUMENTS

| 3,859,349 A | * | 1/1975 | Cody | 562/580 |
| 5,681,728 A | * | 10/1997 | Miao | 435/136 |
| 2005/0020853 A1 | * | 1/2005 | Kuroda et al. | 562/580 |

FOREIGN PATENT DOCUMENTS

| EP | 0393818 A1 | 10/1990 |
| JP | 49-124025 | 11/1974 |
| JP | 63-289020 A | 11/1988 |
| JP | 2-286090 A | 11/1990 |
| JP | 6-501268 A | 2/1994 |
| JP | 9-135698 A | 5/1997 |
| JP | 10-036310 A | 2/1998 |
| JP | 10-174594 A | 6/1998 |
| JP | 2005-270025 A | 10/2005 |
| WO | WO 92/05138 A1 | 4/1992 |

OTHER PUBLICATIONS

Office Action issued in corresponding Korean Patent Application No. 10-2008-7012116 dated Feb. 25, 2010.
Office Action issued in corresponding Chinese Application No. 200680036117.9 dated Jul. 20, 2012.

* cited by examiner

*Primary Examiner* — Sudhakar Katakam
(74) *Attorney, Agent, or Firm* — Buchanan Ingersoll & Rooney PC

(57) ABSTRACT

Glycolic acid having a high purity is obtained by subjecting glycolic acid or a glycolic acid solution containing contaminants to double-chamber electrodialysis combined with one or more treatments selected from among treatment with an activated carbon, treatment with an ion exchange resin, concentration treatment and cooling crystallization.

29 Claims, 3 Drawing Sheets

PROCESS FOR PRODUCING GLYCOLIC ACID

TECHNICAL FIELD

The present invention relates to a process for producing glycolic acid having a high purity.

BACKGROUND ART

A glycolic acid (α-hydroxyacetic acid) has hitherto been used as a general purpose chemical product such as a detergent for boiler scale or the like. However, in recent years, it has been paid attention to as a raw material of polyglycolic acid useful as a material for cosmetics, a biodegradable polymer or a polymer for medical applications. For this reason, there has been increased demand to supply glycolic acid having a high purity at low cost.

A glycolic acid of the class which has been currently put on the market and industrially used is produced by the carbonylation reaction of formaldehyde and water in the presence of glycolic acid and sulfuric acid. The obtained crude glycolic acid has been purified through multi-stage steps such as decolorization by activated carbon treatment, removal of sulfuric acid by an anion exchange resin, removal of low-boiling contaminants by live steam stripping and removal of metallic contaminants by a cation exchange resin (Patent Document 1).

However, the glycolic acid obtained according to the method as described in Patent Document 1 contains not a little contaminants so that it has a problem as a raw material for cosmetics or a raw material for polymers in terms of the purity. For example, organic acids such as oxalic acid, formic acid and the like contaminate in the glycolic acid in some cases. When the glycolic acid is used as a raw material for polymers, even though these contaminants are contained in a very small quantity, a dehydrative condensation reaction of glycolic acid is inhibited and a high molecular weight of glycolic acid is relatively suppressed. Furthermore, a component for coloring polyglycolic acid into a black color is also contained in the contaminants. Furthermore, one of contaminants, methoxyacetic acid, is a compound that is suspected of carcinogenesis, and it is not desirable that methoxyacetic acid is contained in packing materials of cosmetics, food or drink.

In order to enhance the purity of glycolic acid, there has been disclosed a method including adding glycolic acid having a relatively high purity in a small amount as a seed crystal to the glycolic acid of an industrial class obtained in the foregoing purification method and carrying out cooling crystallization at 5 to −18 degree centigrade for obtaining glycolic acid with a smaller amount of contaminants (Patent Document 2). According to the method described in Patent Document 2, there has been described that glycolic acid having a purity of 99% or more may be obtained. However, there is a problem in that the yield is remarkably low (the yield is 6.6% at 5 degree centigrade).

Meanwhile, there has been described a technology that, when organic acid is produced according to the fermentation method by a microorganism, electrodialysis is conducted by an ion exchange membrane, a chelating resin treatment is performed after the electrodialysis, and a water-splitting electrodialysis is conducted by the ion exchange membrane after the chelating resin treatment to respectively collect organic acid and alkali (Patent Document 3).

However, in the Patent Document, there has been no description on useful polyglycolic acid as a material for cosmetics, a biodegradable polymer or a polymer for medical applications, and a raw material glycolic acid for obtaining the polyglycolic acid. Furthermore, when the glycolic acid obtained according to the method described in Patent Document 3 is also used as a raw material, the contaminants are not sufficiently removed, and a high molecular weight of the thus-obtained polyglycolic acid is suppressed.

Patent Document 1: U.S. Pat. No. 3,859,349
Patent Document 2: Japanese PCT International Patent Laid-open No. 1994-501268
Patent Document 3: Japanese Patent Laid-open No. 1997-135698

DISCLOSURE OF THE INVENTION

There have been defects in the conventional methods for producing glycolic acid such that the purity is low regardless of the fact that the purification step is very complicated and inefficient, and the yield of the glycolic acid is remarkably lowered for increasing the cost when high purity glycolic acid is obtained. Furthermore, when glycolic acid according to the conventional method has been used as a raw material, the physical properties of the obtained polyglycolic acid could not be satisfied either.

In order to solve the above object, the present inventors have conducted an extensive study and as a result, have found that a process for producing glycolic acid obtained by electrodialysis combined with at least one or more treatments selected from among activated carbon treatment, ion exchange resin treatment and cooling crystallization is capable of producing glycolic acid having a much higher purity at low cost and in large quantities as a raw material of polyglycolic acid useful as a material for cosmetics, a biodegradable polymer or a polymer for medical applications.

Furthermore, the present inventors have conducted an extensive study and as a result, have found the identity of contaminants in the glycolic acid which influence very badly on the physical properties of the polyglycolic acid and the concentration thereof when polyglycolic acid or the like is produced from the glycolic acid.

That is, the present invention is specified by the matters described below.

[1] A process for producing glycolic acid including carrying out 3 to 5 kinds of steps selected from the group consisting of the following steps (a1), (a2), (b), (c) and (d) (but, the step (a2) must be employed) for a solution containing a glycolate one or two or more times in any order, (a1) step for electrodialyzing with anion exchange membrane and cation exchange membrane;

(a2) step for water-splitting electrodialysis;
(b) step for cooling crystallization;
(c) step for treatment with an activated carbon; and
(d) step for treatment with an ion exchange resin.

[2] The process for producing glycolic acid as set forth in [1], in which the kinds and order of the following steps are any one of (a1)(a2)(b), (c)(a2)(b), (c)(a2)(d)(c) or (c)(a2)(c)(d) for the solution containing the glycolate, (a1) step for electrodialyzing with an anion exchange membrane and a cation exchange membrane;
(a2) step for water-splitting electrodialysis;
(b) step for cooling crystallization;
(c) step for treatment with an activated carbon; and
(d) step for treatment with an ion exchange resin.

[3] A process for producing glycolic acid including carrying out 3 to 5 kinds of steps selected from the group consisting of the following steps (a1), (a2), (b), (c) and (d) (but, the step (a2) must be employed) one or two or more times in any order, and subsequently carrying out the step (b) one or two or more times for the solution containing the glycolate, (a1) step for electrodialyzing with the anion exchange membrane and the cation exchange membrane;
(a2) step for water-splitting electrodialysis;
(b) step for cooling crystallization;
(c) step for treatment with the activated carbon; and
(d) step for treatment with the ion exchange resin.

[4] The process for producing the glycolic acid as set forth in [3], in which the kinds and order of the following steps are any one of (a1)(c)(a2)(b), (a1)(a2)(d)(b), (a1)(c)(a2)(d)(b) or (c)(a2)(d)(b) for the solution containing the glycolate, (a1) step for electrodialyzing with the anion exchange membrane and the cation exchange membrane;
(a2) step for water-splitting electrodialysis;
(b) step for cooling crystallization;
(c) step for treatment with the activated carbon; and
(d) step for treatment with the ion exchange resin.

[5] The process for producing glycolic acid as set forth in any one of [1] to [4], in which the step (a1) is a step for obtaining the glycolate solution by supplying the glycolate solution to a desalination chamber of an electrodialysis device having desalination chambers and concentrating chambers formed by alternately arranging anion exchange membranes and cation exchange membranes between electrodes for conducting electrodialysis, and transmitting a glycolic acid anion and a monovalent cation from said ion exchange membrane; and the step (a2) is a step for obtaining the glycolic acid solution by supplying the glycolate solution after the step (a1) treatment or after the step (c) treatment as it is or via an optional step to the acid chamber of a water-splitting electrodialysis device having acid chambers and base chambers formed by alternately arranging bipolar membranes and cation exchange membranes, and acidifying the glycolic acid anion by electrolysis of water through the bipolar membrane.

[6] The process for producing glycolic acid as set forth in any one of [1] to [5], in which a step (e) for concentration is carried out just before the step (b).

[7] The process for producing glycolic acid as set forth in any one of [1] to [6], containing a step for obtaining the solution containing the glycolate by oxidizing an ethylene glycol.

[8] The process for producing glycolic acid as set forth in any one of [1] to [7], in which the solution containing the glycolate is obtained by bringing a microorganism having the ability to produce a glycolic acid by oxidizing the an ethylene glycol into contact with the ethylene glycol in the presence of oxygen.

[9] The process for producing glycolic acid as set forth in [8], in which said microorganism belongs to the genus *Escherichia*.

[10] The process for producing glycolic acid as set forth in any one of [1] to [9], in which the molar ratio of the ethylene glycol to a purified glycolic acid is less than 0.1%.

[11] The process for producing glycolic acid as set forth in any one of [1] to [10], in which the concentration of the ethylene glycol in the solution containing the glycolate is less than 5% as a molar ratio based on the glycolate.

[12] The process for producing the glycolic acid as set forth in any one of [1] to [11], in which the glycolic acid with the total concentration of the counter cation to the glycolic acid other than hydrogen ion of from 0 to 5 ppm is obtained.

[13] The process for producing the glycolic acid as set forth in any one of [1] to [12], in which the step (a1) is a step for electrodialyzing with a double-chambered electrodialysis device comprised the anion exchange membrane and the cation exchange membrane, and the step (a2) is a step for water-splitting electrodialysis with a double-chambered water-splitting electrodialysis device.

[14] A glycolic acid obtained by the process as set forth in any one of [1] to [13].

[15] A polyglycolic acid made from the glycolic acid obtained by the process as set forth in any one of [1] to [13] as a raw material.

[16] A polyglycolic acid obtained by ring-opening polymerization or polycondensation via a cyclic ester using the glycolic acid obtained by the process as described in any one of [1] to [13] as a raw material.

[17] A glycolic acid copolymer obtained by polycondensation of the glycolic acid obtained according to the process as set forth in any one of [1] to [13] with a compound having one each of a hydroxyl group and a carboxylic acid group or any two of hydroxyl groups or carboxylic acid groups as a functional group in a molecule as raw materials.

[18] An aqueous glycolic acid solution obtained by acidifying an ammonium glycolate using an aqueous solution of an ammonium glycolate as a starting material, wherein the concentration of an ammonium ion in the aqueous solution is not more than 5 ppm based on the glycolic acid.

[19] The aqueous glycolic acid solution as set forth in [18], wherein the aqueous solution of the ammonium glycolate is obtained by the microorganism having the ability to produce the glycolic acid by oxidizing the ethylene glycol.

[20] The aqueous glycolic acid solution as set forth in [19], wherein said microorganism belongs to the genus *Escherichia*.

[21] The aqueous glycolic acid solution as set forth in [18], wherein the acidification of the ammonium glycolate is conducted by the water-splitting electrodialysis treatment of the aqueous solution of the ammonium glycolate.

[22] A glycolic acid obtained from the aqueous glycolic acid solution obtained by acidifying an ammonium glycolate using an aqueous solution of an ammonium glycolate as a starting material, wherein the concentration of an ammonium ion in the glycolic acid is not more than 5 ppm based on the glycolic acid.

[23] The glycolic acid as set forth in [22], wherein the aqueous solution of the ammonium glycolate is obtained by the microorganism having the ability to produce the glycolic acid by oxidizing the ethylene glycol.

[24] The glycolic acid as set forth in [23], wherein said microorganism belongs to the genus *Escherichia*.

[25] The glycolic acid as set forth in [22], wherein the acidification of ammonium glycolate is conducted by the water-splitting electrodialysis treatment of the aqueous solution of the ammonium glycolate.

According to the process for producing the glycolic acid of the present invention, the glycolic acid with small contaminants may be produced in less steps and the glycolic acid having a high purity which may be used as a raw material for polymers may be industrially produced at low cost. By using the glycolic acid obtained by the process as a raw material, a (co)polymer of polyglycolic acid and the like having excellent in the physical properties such as high molecular weight, color and the like may be obtained.

BRIEF DESCRIPTION OF THE DRAWINGS

The aforementioned objects and other objects, characteristics and advantages become further clear by the appropriate embodiments to be described below and the following drawings accompanied thereto.

BEST MODE FOR CARRYING OUT THE INVENTION

Figure 1:
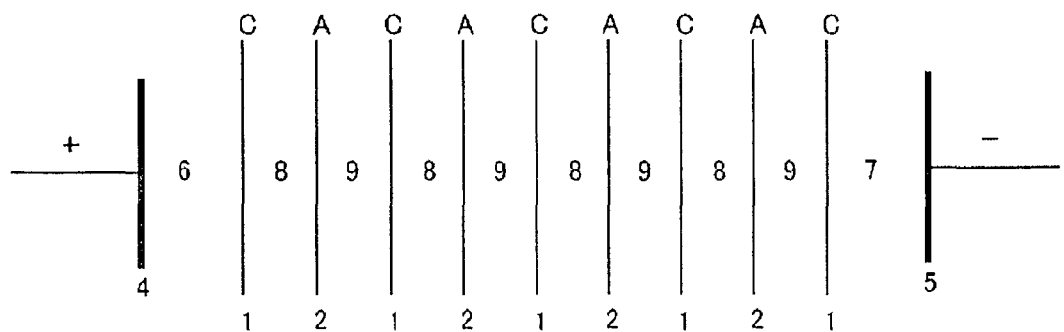
FIG. 1 is a schematic view of the double-chamber anion/cation exchange membrane electrodialysis device to be used in the present invention.

The present invention will be illustrated in detail below.

(Production of a Solution Containing a Glycolate)

In the present invention, "a solution containing a glycolate" refers to a state that a mixture of glycolate or glycolic acid and glycolate is mixed with an optional solvent. Incidentally, the optional solvent mentioned herein more specifically refers to water. However, organic matters such as alcohols and the like, or inorganic salts such as phosphoric acid, sodium chloride and the like, or third components such as protein, fungus body and the like may be present in water regardless of the size of its abundance ratio. Furthermore, as a counter ion of the glycolate, an optional cation such as ammonium ion, sodium ion, potassium ion, magnesium ion, calcium ion or the like may be present regardless of its concentration.

In the present invention, as a process for producing a solution containing a glycolate before the purification to be supplied, any known processes may be used.

Furthermore, using a microorganism having nitrilase activity or nitrile hydratase activity as a catalyst, a solution containing a glycolate obtained by hydrating glycolonitrile may also be suitably used. For example, there may be exemplified a process including adding a microorganism having nitrilase activity to a potassium phosphate buffer solution containing glycolonitrile for obtaining ammonium glycolate by hydrating glycolonitrile (International Publication No. WO 2002/068659), a process including adding a microorganism having nitrile hydratase activity to an aqueous solution containing glycolonitrile for obtaining a glycolic acid amide by hydrating glycolonitrile and further obtaining ammonium glycolate from the glycolic acid amide by heating the solution, and the like. Incidentally, the microorganism having nitrilase activity or nitrile hydratase activity mentioned herein refers to a generic term of a microorganism having the ability to produce glycolic acid from glycolonitrile or a microorganism having the acquired or enhanced ability to produce glycolic acid from glycolonitrile by using any means.

Furthermore, the present invention may also be applied to a solution containing a glycolate obtained by oxidation of ethylene glycol. In particular, a process for generating a solution containing a glycolate under from neutral to alkaline conditions is preferable. For example, there may be exemplified a process including adding a palladium on activated carbon powder catalyst to distilled water containing ethylene glycol, properly adding sodium hydroxide for maintaining the pH at 8 to 10 and blowing air to obtain a solution of glycolic acid sodium salt by oxidation of ethylene glycol (Japanese Patent Laid-open No. 1979-132519), a process for obtaining a glycolic acid solution by hydrolyzing methyl glycolate obtained by reacting ethylene glycol and methanol with oxygen in the presence of an $Au/TiO_2$—$SiO_2$ catalyst (Japanese Patent Laid-open No. 2004-43386) and the like.

In particular, a solution containing a glycolic acid and/or a glycolate obtained by bringing a microorganism producing glycolic acid by oxidation of ethylene glycol into contact with ethylene glycol in the presence of oxygen is the most suitably used.

In the present invention, the microorganism producing glycolic acid by oxidation of ethylene glycol refers to a generic term of a microorganism having the ability to produce glycolic acid from ethylene glycol or a microorganism having the acquired or enhanced ability to produce glycolic acid from ethylene glycol by using any means.

Herein, examples of the microorganism having the acquired or enhanced ability to produce glycolic acid from ethylene glycol include a microorganism having an enzyme catalyzing a reaction from ethylene glycol to glycolaldehyde and an enzyme catalyzing a reaction from glycolaldehyde to glycolic acid, or a microorganism having the imparted or enhanced activity of such an enzyme by any method. Examples of such an enzyme include lactoaldehyde reductase and lactoaldehyde dehydrogenase. By imparting the enzyme activity to the wild-type microorganism without having the enzyme activity at all by a method such as gene recombination or the like, the enzyme activity is significantly enhanced as compared to the wild-type microorganism so that the ability to produce glycolic acid from ethylene glycol is acquired or enhanced. Concrete examples of such a microorganism include, though not restricted to, gene recombined *Escherichia coli* as illustrated in Examples.

These microorganisms may be produced, for example, by using a process for introducing a gene coding the enzyme to the wild-type microorganism using a technique of gene recombination or the like. Methods such as preparation of genome DNA, preparation of plasmid, cutting and connecting of DNA, transformation, PCR (Polymerase Chain Reaction), design of oligonucleotide used as a primer, synthesis thereof and the like may be conducted in a usual method well known to the skilled person in the art. These methods are described in Sambrook, J., et. al., "Molecular Cloning A Laboratory Manual, Second Edition," Cold Spring Harbor Laboratory Press, (1989) and the like.

In the present invention, as the medium to be used for the culture of microorganisms, a medium containing carbon source, nitrogen source, inorganic ion and as needed traces of other organic components may be used. As the carbon source, saccharides such as glucose, fructose, molasses and the like; organic acids such as fumaric acid, citric acid, succinic acid and the like; and alcohols such as methanol, ethanol, glycerol and the like are properly used. As the nitrogen source, inorganic nitrogen sources such as organic ammonium salts, inorganic ammonium salts, ammonia gas, ammonia water and the like; and organic nitrogen sources such as protein hydrolysates and the like; and others are properly used. As the inorganic ion, magnesium ion, phosphate ion, potassium ion, iron ion, manganese ion and others are properly used as required. As traces of organic components, vitamin, amino acid or the like and yeast extracts containing these, peptone, corn steep liquor, casein digest and others are properly used.

Incidentally, as the medium to be used for the present invention, a liquid medium is preferably used in the light of the industrial production.

In the present invention, as the conditions for the culture of microorganisms, for example, when the microorganism is cultured while properly controlling the pH and temperature in a pH range of 5 to 8, in a temperature range of 25 to 40 degree centigrade under aerobic conditions, the time required for the culture may be within 50 hours.

In the present invention, "bringing a microorganism into contact with ethylene glycol in the presence of oxygen" refers to a state capable of sufficiently bringing ethylene glycol, a microorganism and oxygen into contact with one another by adding ethylene glycol and cultured microorganism to a liquid capable of adding ethylene glycol, for example, a buffer solution such as a potassium phosphate buffer solution and the like or a medium used for the culture of the microorganism and pure water, blowing air or oxygen using a sparger, a single tube or the like, and stirring by using a stirring blade such as a disc turbine or the like, or refers to a procedure to achieve the state.

Herein, in the present invention, according to the aforementioned state or procedure, an action of obtaining a solution containing a glycolate from ethylene glycol is defined as a "reaction" hereinafter and a solution containing a glycolate obtained by the "reaction" is defined as a "reaction solution."

As the reaction solution to be used for a reaction to produce glycolic acid according to the present invention, a liquid containing ethylene glycol may be used. Examples thereof include a buffer solution such as a potassium phosphate buffer solution and the like or a medium used for the culture of the microorganism and pure water.

Upon the reaction to produce the glycolic acid of the present invention, as the reaction condition, for example, the reaction is preferably carried out while appropriately controlling the pH and temperature in a pH range of 6 to 9, in a temperature range of 20 to 40 degree centigrade.

As a method for properly controlling the pH, there may be exemplified a process for timely feeding an aqueous alkali solution sufficiently capable of neutralizing the generated glycolic acid.

Examples of the aqueous alkali solution to be used include an aqueous solution of sodium hydroxide, an aqueous solution of potassium hydroxide, an aqueous solution of ammonia and the like. Furthermore, when the glycolic acid is timely neutralized and reacted in this manner, the glycolic acid is obtained as a glycolate.

As a method for removing fungus body in the reaction solution, for example, a method for removing fungus body from the reaction solution by centrifugation and the like may be adopted.

In particular, for carrying out the present invention, ethylene glycol is contained in the solution containing a glycolate in some cases. Even though a purification treatment to be described later is carried out, depending on concentration of the ethylene glycol, the ethylene glycol may not be completely removed in some cases. Herein, since ethylene glycol has two hydroxyl groups as a functional group, when the glycolic acid is polymerized for obtaining polyglycolic acid, the molar balance between a carboxyl group and a hydroxyl group before the initiation of polymerization is changed. As a result, the ethylene glycol functions as a polymerization inhibitor. Accordingly, when polyglycolic acid having a much higher molecular weight is produced, it is important to reduce the concentration of ethylene glycol in the solution containing a glycolate as much as possible and to conduct various purification procedures to be described later using such ethylene glycol for reducing the concentration of ethylene glycol contained in the glycolic acid to be obtained after the purification as much as possible. Furthermore, the present inventors have found a phenomenon that, in the glycolate solution containing the ethylene glycol, even in the low temperature, a condensate of ethylene glycol and glycolic acid is spontaneously generated and time-dependently increased.

Since this condensate of ethylene glycol and glycolic acid also has only two hydroxyl groups as a functional group, the condensate functions as a polymerization inhibitor as well as ethylene glycol, when the glycolic acid is polymerized for obtaining polyglycolic acid.

From the above fact, in the present invention, the concentration of ethylene glycol contained in the solution containing a glycolate at a step before various purification treatments to be described later are performed, and the concentration of ethylene glycol in the glycolic acid after various purification treatments to be described later are performed are preferably reduced as much as possible. More specifically, in the solution containing a glycolate at a step before various purification treatments to be described later are performed, the molar ratio to the glycolate may be reduced down to less than 5% and more preferably less than 1%. In the glycolic acid after various purification treatments to be described later are performed, the molar ratio to the glycolic acid may be reduced down to less than 0.1% and more preferably less than 0.02%.

(a1) Step for Electrodialyzing with an Anion Exchange Membrane and a Cation Exchange Membrane In the present invention, the "electrodialysis device" refers to an electrodialysis device formed by alternately arranging any two kinds of a cation exchange membrane, an anion exchange membrane and a bipolar membrane. In the present invention, the electrodialysis procedure conducted by using this device is defined as an "step for electrodialysis." Furthermore, as the electrodialysis device to be used in the present invention, there is an "anion/cation exchange membrane electrodialysis device" obtained by alternately arranging cation exchange membranes and anion exchange membranes for forming concentrating chambers and desalination chambers, and as a typical example, there may be cited a "double-chambered electrodialysis device comprised an anion exchange membrane and a cation exchange membrane." Then, in the present invention, the electrodialysis procedure using the "double-chambered electrodialysis device comprised an anion exchange membrane and a cation exchange membrane" is defined as a "step for electrodialyzing with the anion exchange membrane and the cation exchange membrane." More specifically, a typical example includes a "step for electrodialyzing with a double-chambered electrodialysis device comprised the anion exchange membrane and the cation exchange membrane."

As an electrode of the anion/cation exchange membrane electrodialysis device in the present invention, any known electrodes may be used. That is, as the anode, platinum, titanium/platinum, carbon, nickel, ruthenium/titanium, iridium/titanium and the like may be used. Furthermore, as the cathode, iron, nickel, platinum, titanium/platinum, carbon, stainless steel and the like may be used. Furthermore, as the structure of the electrode, any known structures may be adopted. Examples of the general structure include a mesh-shaped structure, a lattice-shaped structure and the like.

Furthermore, in the present invention, as the cation exchange membrane and anion exchange membrane of electrodialysis device with the anion/cation exchange membrane, any conventionally-known membranes may be used.

Furthermore, in the present invention, the anion/cation exchange membrane electrodialysis device is constructed by alternately arranging anion exchange membranes and cation exchange membranes between a positive electrode and a negative electrode for forming concentrating chambers and desalination chambers.

FIG. 1 illustrates a schematic view of the typical embodiment of the anion/cation exchange membrane electrodialysis device used in the present invention.

That is, in FIG. 1, the anion/cation exchange membrane electrodialysis device is constructed such that two kinds of cation exchange membranes C and anion exchange membranes A are alternately arranged as a membrane between a positive electrode 4 and a negative electrode 5 for forming two chambers of concentrating chambers 8 and desalination chambers 9. A gap 6 between the cation exchange membrane C and the positive electrode 4, and a gap 7 between the cation exchange membrane C and the negative electrode 5 are filled with an electrode solution.

As for the structure of the aforementioned anion/cation exchange membrane electrodialysis device, any known structures may be adopted.

In the present invention, as the electrodialysis method using the aforementioned electrodialysis device comprised the anion exchange membrane and the cation exchange membrane, a method including conducting electrodialysis by placing an external tank (not illustrated) to be supplied the solution to respective chambers of the concentrating chambers 8 and the desalination chambers 9 while circulating the solution between respective chambers and the external tank may be suitably adopted.

When the glycolic acid solution is supplied to the desalination chamber 9 for carrying out the anion/cation exchange membrane electrodialysis, the purified glycolate is concentrated at the concentrating chamber 8. At this time, there are contaminants such as protein, amino acid, pigments, organic acids such as oxalic acid, glyoxylic acid, formic acid, acetic acid and the like, or inorganic salts present in the glycolic acid solution. However, the electrodialysis with the anion/cation exchange membrane, those that are transferred to the concentrating chamber 8 and concentrated are mainly the glycolate and inorganic salts.

In the present invention, it is suitable that the temperatures of various solutions at the time of the step for electrodialyzing with anion exchange membrane and cation exchange membrane are usually in the range of 5 to 70 degree centigrade and preferably in the range of 20 to 50 degree centigrade.

(c) Step for Treatment with an Activated Carbon

In the present invention, as the activated carbon to be used when the activated carbon treatment is performed for the solution containing a glycolate, any known carbons may be used. Or, the shape thereof may be a powder-like shape, a granule-like shape or the like and is not particularly limited. The amount of use is preferably reduced as much as possible from the economical point of view. However, specifically, the amount is preferably not more than 20 weight % based on the solution containing a glycolate which the activated carbon is added. Furthermore, the amount is more suitably from 1 to 12.5 weight %. A treatment method is suitably adopted such that the contact temperature and the time are suitably 10 to 30 degree centigrade and 15 to 60 minutes. As the contact method, for example, a batch method, a column filling method or the like is adopted.

(a2) Step for Water-Splitting Electrodialysis

In the present invention, in order to change from the glycolate to the glycolic acid, a "water-splitting electrodialysis device" is used. The device is an electrodialysis device having acid chambers and base chambers which is formed by alternately arranging bipolar membranes and cation exchange membranes. As a typical example, a "a double-chambered water-splitting electrodialysis device" may be cited. In the present invention, the electrodialysis procedure using the "water-splitting electrodialysis device" is defined as a "step for water-splitting electrodialysis." Then, further specifically, as a typical treatment, a "step for water-splitting electrodialysis with a double-chambered water-splitting electrodialysis device" may be typically exemplified.

In the step for water-splitting electrodialysis, the obtained glycolic acid solution is subjected to the step for water-splitting electrodialysis using the water-splitting electrodialysis device for recovering glycolic acid and alkali respectively.

Namely, the glycolic acid solution is provided to the water-splitting electrodialysis device using the bipolar membrane and the cation exchange membrane for performing the step for water-splitting electrodialysis so that glycolic acid is obtained from the acid chamber and alkali is obtained from the base chamber respectively.

As the bipolar membrane in the present invention, any conventionally-known bipolar membranes, that is, any known bipolar membranes having a structure attached the cation exchange membrane and an anion exchange membrane, may be used.

Furthermore, in the present invention, as the cation exchange membrane of the water-splitting electrodialysis device, any known cation exchange membranes may be used.

In the present invention, the water-splitting electrodialysis device is constructed by alternately arranging bipolar membranes and cation exchange membranes between a positive electrode and a negative electrode for forming acid chambers and base chambers.

Figure 2:
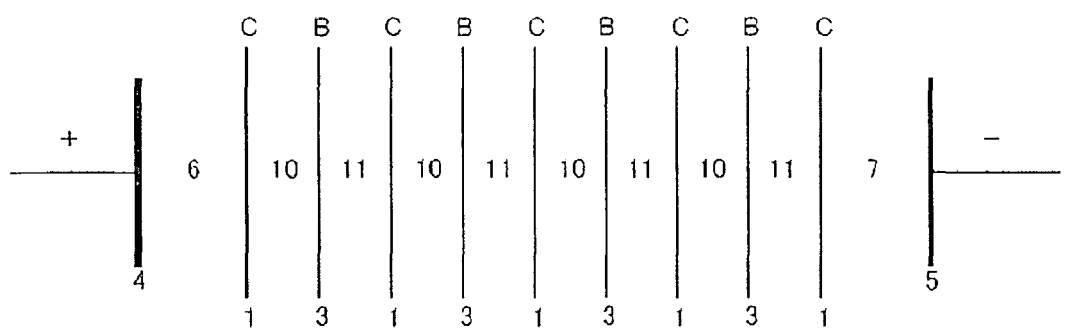
FIG. 2 is a schematic view of the double-chamber water-splitting electrodialysis device to be used in the present invention.

FIG. 2 illustrates a schematic view of the typical embodiment of the water-splitting electrodialysis device used in the present invention.

That is, in FIG. 2, the water-splitting electrodialysis device is constructed such that two kinds of bipolar membranes B and cation exchange membranes C are alternately arranged between a positive electrode 4 and a negative electrode 5 for forming two chambers of acid chambers 11 and base chambers 10. A gap 6 between the cation exchange membrane C and the positive electrode 4, and a gap 7 between the cation exchange membrane C and the negative electrode 5 are filled with an electrode solution. Herein, a chamber between the anion exchanger side of the bipolar membrane B and the cation exchange membrane C is the base chamber 10, while a chamber between the cation exchanger side of the bipolar membrane B and the cation exchange membrane C is the acid chamber 11.

As for the structure of the aforementioned water-splitting electrodialysis device, any known structures may be adopted.

In the present invention, as the step for water-splitting electrodialysis using the aforementioned water-splitting electrodialysis device, a method including conducting electrodialysis by placing an external tank (not illustrated) to be supplied the solution to respective chambers in the acid chambers 11 and the base chambers 10 while circulating the solution between respective chambers and the external tank may be suitably adopted.

When the aforementioned glycolic acid solution is supplied to the acid chamber 11 for carrying out electrodialysis, the glycolate of the acid chamber 11 is electrically connected and at the same time converted to glycolic acid.

Namely, the cation of the glycolate introduced into the acid chamber 11 passes through the cation exchange membrane C and transferred to the base chamber 10, and at this time, is combined with OH ion generated from the bipolar membrane B to be a base. Furthermore, in the acid chamber 11, proton generated from the bipolar membrane B and the glycolic acid anion are combined to be a nondissociative glycolic acid which remains in the acid chamber 11 as it is.

In the present invention, it is suitable that the temperatures of various solutions upon the step for water-splitting electrodialysis are usually in the range of 5 to 70 degree centigrade and preferably in the range of 20 to 50 degree centigrade.

As described above, according to the step for water-splitting electrodialysis, the glycolate is decomposed so that glycolic acid and alkali may be separated for recovering the glycolic acid.

Incidentally, the separated alkali may be reused as a neutralizing agent in an organic acid fermentation such as glycolic acid or the like.

According to the aforementioned step for electrodialyzing with anion exchange membrane and cation exchange membrane and step for water-splitting electrodialysis, glycolic acid having a higher purity than the commercial/industrial class may be obtained.

That is, the purity of the glycolic acid of the commercial/industrial class is about 82%, while the purity of the glycolic acid obtained by the step for electrodialyzing with anion exchange membrane and cation exchange membrane and the step for water-splitting electrodialysis is about 98%.

(d) Step for Treatment with an Ion Exchange Resin

In the present invention, for the ion exchange resin treatment, any known cation exchange resins may be used. However, in particular, a cation exchange resin having a strong acidic ion exchange group is suitably used. As such a strong acidic ion exchange group, a sulfonic acid group may be cited. The amount of use is from 1 to 10 weight % and more suitably from 3 to 5 weight % based on the glycolic acid solution which the cation exchange resin is added. A treatment method is suitably adopted such that the contact temperature and the time are suitably 10 to 30 degree centigrade and for 15 to 60 minutes. As the contact method, for example, a batch method, a column filling method or the like is adopted. According to the procedure, cation such as sodium ion, potassium ion, ammonium ion, calcium ion, magnesium ion and the like may be removed by adsorption so that the concentration of cation remained in the solution after the treatment is not more than 5 ppm based on the glycolic acid.

(e) Step for Concentration

In the present invention, the concentration step is conducted according to the known concentration method.

For example, the heating may be conducted at 20 to 80 degree centigrade and more suitably at 30 to 40 degree centigrade under reduced pressure. However, the present invention is not restricted thereto. According to the concentration treatment, the glycolic acid solution may be concentrated at any concentration, but it may be preferably concentrated at not less than 70 weight % and more preferably from 70 to 85 weight %.

(b) Step for Cooling Crystallization

In the present invention, as the cooling crystallization treatment method, any known methods may be used. However, by performing the concentration treatment mentioned before and cooling the glycolic acid solution concentrated at 70 to 85 weight % at a temperature of from 5 to −25 degree centigrade and more suitably from 4 to −20 degree centigrade, glycolic acid crystals may be obtained with a high yield of 32% to 75%. In particular, there is no need to add pure glycolic acid as a seed crystal, but the pure glycolic acid may also be added. Further, by allowing the solution to stand without stirring during cooling, it is possible to obtain crystals in which a crystal particle diameter is much larger, the purity is high, and filtering and recovery are easy. As the material of the vessel used for performing the cooling crystallization, any known materials such as glass, SUS or the like may be used.

As a method for recovering the obtained crystals, known methods for separating crystals from a mother liquor may be used. For example, the crystals and filtrate may be separated by using a batch pressure filter represented by a filter press, a vacuum belt filter or a leaf filter, or a centrifuge represented by a screw demayter, though not restricted thereto. Furthermore, before the separated crystal cake is dried, it may be washed with various solvents such as water, an aqueous glycolic acid solution, alcohol and the like.

As a method for drying the recovered crystal, any known methods may be used. For example, however, it is suitable to vacuum dry in a vacuum dryer at 10 to 25 degree centigrade for 16 to 24 hours.

In the present invention, the solution containing a glycolate may be subjected to 3 to 5 kinds of steps including at least the step (a2) selected from the group consisting of the aforementioned step (a1), step (a2), step (b), step (c) and step (d) in any order one or two or more times.

According to such a process for producing the glycolic acid of the present invention, glycolic acid with small contaminants may be produced in less steps, and glycolic acid having a high purity capable of being used as a raw material for polymers may be industrially produced at low cost. Incidentally, "subjected to 3 to 5 kinds of steps in an optional order one or two or more times" in the present invention includes any of (A) an embodiment of selecting, for example, step a1, step a2 and step b and performing all selected steps such as step b→step a1 →step a2 in an optional order one time, which is repeatedly performed one or two or more times, and (B) an embodiment of selecting, for example, step a1, step a2 and step b and repeatedly performing each selected step such as step b→step b→step a1 →step a2 →step a1 at optionally several times.

Furthermore, the process for producing the glycolic acid of the present invention is preferably performed in any of the following orders for the solution containing a glycolate:

(1) step (a1), step (a2), step (b);
(2) step (c), step (a2), step (b);
(3) step (c), step (a2), step (d), step (c); and
(4) step (c), step (a2), step (c), step (d).

By performing the process for producing the glycolic acid in such an order, the glycolic acid having a much higher purity may be produced.

Furthermore, from the viewpoint of producing glycolic acid having a high purity, it is also preferable that the steps are conducted in the aforementioned order, and subsequently the (b) step for cooling crystallization is conducted one or two or more times.

In the present invention, as an embodiment of performing the (b) step for cooling crystallization lastly, a solution containing a glycolate is preferably subjected to any of the following steps in one of the following orders, from the viewpoint of producing glycolic acid having a high purity:

(5) step (a1), step (c), step (a2), step (b);
(6) step (a1), step (a2), step (d), step (b);
(7) step (a1), step (c), step (a2), step (d), step (b); or
(8) step (c), step (a2), step (d), step (b).

Furthermore, just before the (b) step for cooling crystallization, it is preferable to perform the (e) concentration step of the glycolic acid solution. In this manner, the (b) step for cooling crystallization may be efficiently performed.

According to the process for producing the glycolic acid including such steps of the present invention, it is possible to obtain glycolic acid having a high purity in which the molar ratio of ethylene glycol contained in the glycolic acid to the glycolic acid is reduced down to less than 0.1% and preferably less than 0.02%. By using such glycolic acid, it is possible to produce a (co)polymer of polyglycolic acid and the like in which the molecular weight is higher than the conventional one and coloring is reduced.

Furthermore, in the glycolic acid obtained by the process for producing the glycolic acid of the present invention, the total concentration of a counter cation other than hydrogen ion such as ammonium ion or the like is reduced down to not more than 5 ppm and preferably 0 to 1 ppm based on the glycolic acid. Therefore, coloring of the polyglycolic acid obtained by using the glycolic acid as a raw material is reduced and the transmittance is enhanced.

By using the glycolic acid obtained in the production process of the present invention and performing the polymerization according to the method to be described later, a polyglycolic acid or glycolic acid copolymer with less coloring and having a high molecular weight may be obtained.

One example of the processes for producing polyglycolic acid include a polymerization method of glycolic acid in which includes a two-stage step of,

[first step]: a step for obtaining an oligomer by dehydrating the aqueous glycolic acid solution in an ordinary pressure or under reduced pressure at a temperature of from 100 degree centigrade or more to 160 degree centigrade or less and having a weight average molecular weight of from 1,000 to 10,000; and

[second step]: a step for drying in the air the oligomer obtained in the first step, and solid polymerization in an inert gas flow, at a temperature of from 180 degree centigrade or more to 230 degree centigrade or less to obtain polymer having a weight average molecular weight of not less than 30,000. But the present invention is not restricted thereto.

Further, the glycolic acid copolymer may be produced by a known method, or it may be obtained by subjecting glycolic acid and a compound having one each of a hydroxyl group and a carboxylic acid group or any of two groups thereof as a functional group in a molecule as a raw material to polycondensation. Examples of the aforementioned compound include isophthalic acid, ethylene glycol, diethylene glycol and the like.

EXAMPLES

The present invention is now illustrated in detail below with reference to Examples. However, the present invention is not restricted to these Examples. Incidentally, in Examples 1 to 8, a series of steps to obtain glycolic acid from ammonium glycolate are explained.

As for a method for measuring the concentration of each component according to the present invention, the following method may be cited as a typical example. However, the present invention is not restricted to this method, and any known methods may be adopted.

[Concentration of Glycolic Acid and Concentration of Ethylene Glycol]

Using high performance liquid chromatography (HPLC) manufactured by Hitachi Ltd., the concentrations were quantitatively analyzed with the following settings: column; ULTRON PS-80H (a product of Shinwa Chemical Industries Ltd.), eluent; aqueous perchloric acid solution (pH=2.1), flow rate; 1.0 mL/min. The glycolic acid was detected at a wavelength of 210 nm using UV as a detector. Furthermore, ethylene glycol was detected with the same HPLC at the same settings using a differential thermal refractometer (RI) as a detector.

[Concentration of Cation]

Using ion chromatography manufactured by JASCO Corp., it was quantitatively analyzed with the following settings: column; Shodex IC YK-421 (a product of Showa Denko K. K.), eluent; 3 mM aqueous phosphoric acid solution, flow rate; 1.0 mL/min. Furthermore, an electric conductivity meter was used as a detector.

Example 1

Construction of Lactaldehyde Reductase and Lactoaldehyde Dehydrogenase Co-Expression Vector and a Transformant of the Expression Vector The amino acid sequence of lactaldehyde reductase of *Escherichia coli* and the base sequence of its gene (hereinafter may be simply referred to as fucO) have been already reported (GenBank accession number: M31059). Furthermore, the amino acid sequence of lactoaldehyde dehydrogenase of *Escherichia coli* and the base sequence of a gene (hereinafter may be simply referred to as aldA) have been already reported (GenBank accession number: M64541). In order to acquire fucO, GCTCTAGACGGAGAAAGTCT-TATGATGGCTAACAGAATGATTCTG (Sequence No. 1) and GTGAAGCTTGCATTTACCAGGCGGTATGG (Sequence No. 2) were amplified with a PCR method using the genome DNA of *Escherichia coli* MG1655 strain as a template, and the obtained DNA fragments were digested with restriction enzymes XbaI and HindIII to obtain a fucO fragment of about 1.2 kbp. Furthermore, in order to acquire aldA, CGAATTCCGGAGAAAGTCTTATGTCAG-TACCCGTTCAACATCC (Sequence No. 3) and GCTCTA-GACTCTTTCACTCATTAAGACTG (Sequence No. 4) were amplified with a PCR method using the genome DNA of *Escherichia coli* MG1655 strain as a template, and the obtained DNA fragments were digested with restriction enzymes EcoRI and XbaI to obtain an aldA fragment of about 1.5 kbp. Furthermore, in order to acquire a glyceraldehyde 3-phosphate dehydrogenase (GAPDH) promoter, AAC-GAATTCTCGCAATGATTGACACGATTC (Sequence No. 5) and ACAGAATTCGCTATTTGTTAGTGAATAAAAGG (Sequence No. 6) were amplified with a PCR method using the genome DNA of *Escherichia coli* as a template, and the obtained DNA fragments were digested with a restriction enzyme EcoRI to obtain DNA fragments of about 100 bp which encodes a GAPDH promoter (in the base sequence information of GenBank accession number X02662, described in 397-400). The above-mentioned three DNA fragments were mixed with the fragment obtained by digestion of plasmid pUC18 using restriction enzymes EcoRI and HindIII, ligated using a ligase, and then transformed to an *Escherichia coli* DH5α strain to obtain a transformant which grows on an LB agar plate containing 50 μg/mL of ampicillin. The obtained colony was cultured in an LB liquid medium containing 50 μg/mL of ampicillin at 37 degree centigrade overnight, and a plasmid pGAPfucO-aldA was recovered from the obtained fungus body. This plasmid pGAPfucO-aldA was transformed to an *Escherichia coli* MG1655 strain, and cultured on an LB agar plate containing 50 μg/mL of ampicillin at 37 degree centigrade overnight to obtain a MG1655/pGAPfucO-aldA strain.

Incidentally, the *Escherichia coli* MG1655 strain and *Escherichia coli* DH5α strain may be available from the Amerimay Type Culture Collection.

Example 2

Figure 3:
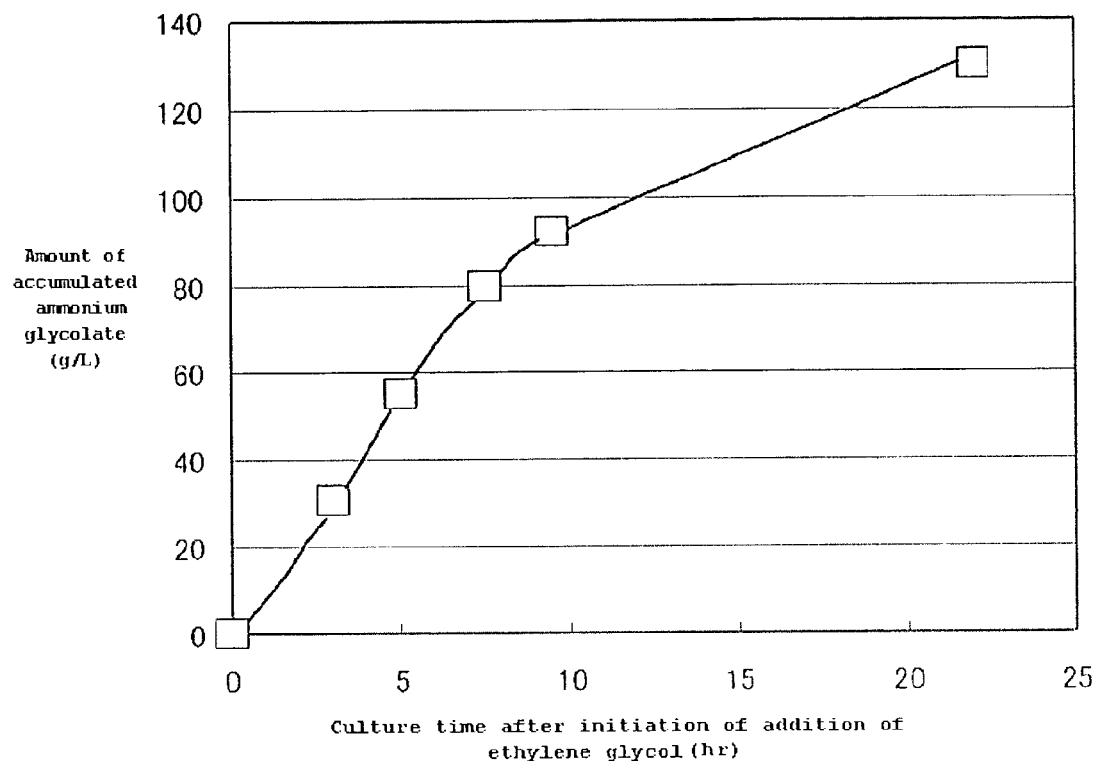
FIG. 3 is a graph illustrating the change with time in the amount of ammonium glycolate accumulated in a reaction solution in Example 2.

Production of Ammonium Glycolate by *Escherichia coli* MG1655/pGAPfucO-aldA Strain The *Escherichia coli* MG1655/pGAPfucO-aldA strain obtained in Example 1 was inoculated into 25 mL of LB Broth, Miller medium (Difco244620) contained in a conical flask, and the overnight culture was carried out with stirring with 120 rpm at a culture temperature of 35 degree centigrade as preculture. Then, the whole amount of the preculture solution was transferred to a 1 L-fermentor (BMJ-01, culture apparatus manufactured by ABLE Corporation) containing 475 g of the medium of the composition shown in Table 1 to carry out the culture. The culture was carried out under the conditions including atmospheric pressure, an aeration rate of 1 vvm, an agitation rate of 800 rpm, a culture temperature of 35 degree centigrade and pH of 7.2 (adjusted with an aqueous ammonia solution). After 24 hours from initiating the culture, ethylene glycol was added thereto at a rate of 5 g/hr for 22 hours. The amount of ammonium glycolate accumulated in the culture was measured with HPLC according to an established method. The results are shown in FIG. 3.

It was confirmed that 129 g/L of ammonium glycolate was accumulated in the *Escherichia coli* MG1655/pGAPfucO-aldA strain for 22 hours. Further, the concentration of the remained ethylene glycol was less than 0.002 mole % based on ammonium glycolate.

TABLE 1

| Medium Composition | |
|---|---|
| Polypepton | 7 g/L |
| Glucose | 30 g/L |
| $Fe_2SO_4$ | 0.09 g/L |
| $K_2HPO_4$ | 2 g/L |
| $KH_2PO_4$ | 2 g/L |
| $MgSO_4 \cdot 7H_2O$ | 2 g/L |
| $(NH_4)_2SO_4$ | 1.5 g/L |

(residue: water)

Example 3

Preparation of the Glycolic Acid Solution by Electrodialyzing with a Double-Chambered Electrodialysis Device Comprised the Anion Exchange Membrane and the Cation Exchange Membrane As the double-chambered electrodialysis device comprised the anion exchange membrane and the cation exchange membrane, it was used a filter press type electrodialysis device in which 10 membranes (total effective membrane area: 550 cm$^2$) each of anion exchange membranes (a product of Astom Co., Ltd., product name: Neosepta ACS) and cation exchange membranes (a product of Astom Co., Ltd., Neosepta CMX) were respectively arranged by turns for forming desalination chambers and concentrating chambers. A tank used for supplying 3 kg of the ammonium glycolate solution obtained in Example 2 to the desalination chambers and a tank used for supplying 1.2 kg of pure water to the concentrating chambers were placed, the ammonium glycolate solution and pure water were supplied and circulated. Incidentally, as an electrode solution, 1.5 kg of a 2% aqueous solution of sulfuric acid was used. Using these devices, electrodialysis was performed at room temperature (about 25 degree centigrade), at a constant voltage of 15V for 11 hours. As a result, 2.3 kg of an ammonium glycolate solution having a concentration of ammonium glycolate of 16.2 weight % was obtained from the concentrating chamber.

Example 4

Activated Carbon Treatment of a Glycolic Acid Solution 119 g of activated carbon Lewatit AF5 (a product of LANXESS) in which moisture was easily wiped up after washing with water was taken in a 1 L beaker. To the beaker was added 5 kg of the ammonium glycolate solution obtained in Example 3. The resulting mixture was stirred at 25 degree centigrade for 15 minutes, and then a supernatant treated by demaytation was transferred to another vessel. The recovered supernatant was vacuum filtered for removing powdered activated carbon particles. By the procedure, organic acid, an organic acid salt, impure protein and a coloring component other than the glycolate were removed. Furthermore, the recovery rate of ammonium glycolate according to the procedure was 98.8%.

Example 5

Preparation of the Glycolic Acid Solution from the Glycolate Solution by Double-Chambered Water-Splitting Electrodialysis Devise As the double-chambered water-splitting electrodialysis device, it was used a filter press type electrodialysis device in which 10 membranes (total effective membrane area: 550 cm$^2$) each of cation exchange membranes (a product of Astom Co., Ltd., product name: Neosepta CMX) and bipolar membranes (a product of Astom Co., Ltd., Neosepta BP-1) were respectively arranged by turns for forming acid chambers and base chambers. A tank used for supplying 2.5 kg of the ammonium glycolate solution obtained in Example 4 to the acid chambers and a tank used for supplying 2.5 kg of pure water to the base chambers were placed, the ammonium glycolate solution and pure water were supplied and circulated. Incidentally, as an electrode solution, 2 kg of a 2% aqueous solution of sulfuric acid was used. Using these devices, electrodialysis was performed at room temperature (about 25 degree centigrade), at a constant voltage of 20V for 10.5 hours. As a result, 2.3 kg of a glycolic acid solution having a concentration of the glycolic acid of 12.3 weight % and a concentration of ammonium ion of 800 ppm was obtained from the acid chamber, while 2.7 kg of ammonia water was obtained from the base chamber.

Example 6

Treatment of a Glycolic Acid Solution by Cation Exchange Resin 80 mL of a cation exchange resin (Dowex 50W-X8-200) was suspended in pure water, filled in a column having a diameter of 2.5 cm, and washed with pure water of 10 times or more in volume. After washed, the glycolic acid solution obtained in Example 5 was penetrated into the column at a flow rate of 7 mL/min by using a constant flow rate pump. The recovered glycolic acid solution was analyzed by ion chromatography and as a result, the concentration of ammonium ion was reduced down to less than the limit of detection (1 ppm) from 800 ppm. Furthermore, the recovery rate of the glycolic acid according to the procedure was 100%.

Example 7

Concentration of the Glycolic Acid Solution 4.5 kg of the glycolic acid solution obtained in Example 6 was concentrated under reduced pressure at 100 mbar, at 30 degree centigrade for 12 hours using a rotary vacuum evaporator (a product of EYELA Co., Ltd.) and as a result, 663 g of a glycolic acid solution having a concentration of the glycolic acid of 78.9 weight % and a concentration of ammonium ion of less than the limit of detection (1 ppm) was obtained.

Example 8

Preparation of Glycolic Acid by Cooling Crystallization 446 g of the glycolic acid solution obtained in Example 7 was maintained at −20 degree centigrade for 16 hours. In the meantime, a large number of hexagonal crystals were generated. A buchner funnel equipped with 5A filter paper (a product of Advantec MFS, Inc.) was attached to a suck bottle, and the crystals were sucked up with a vacuum pump and recovered by suction filtration. The recovered crystals were transferred to a plastic Petri dish having a diameter of 10 cm, and dried under reduced pressure at 26 degree centigrade for 24 hours. The crystals were analyzed and as a result, 254 g of glycolic acid crystals (yield: 72.4%) having a concentration of the glycolic acid of 99.99 weight % and a concentration of ammonium ion of less than the limit of detection (1 ppm) was obtained.

Example 9

Polymerization Evaluation of Glycolic Acid Obtained by Combining Treatment with Double-Chambered Electrodialysis Device, Treatment with Activated Carbon Treatment, Concentration Treatment and Cooling Crystallization Using the *Escherichia coli* MG1655/pGAPfucO-aldA strain described in Example 1, 2 kg of the ammonium glycolate solution (concentration of ammonium glycolate: 12.9 weight %) obtained by the method as described in Example 2 was subjected to treatment with double-chambered electrodialysis device comprised the anion exchange membrane and the cation exchange membrane described in Example 3 to obtain 1.5 kg of an ammonium glycolate solution (concentration of ammonium glycolate: 16.8 weight %). Subsequently, the activated carbon treatment described in Example 4 was conducted to obtain 1.6 kg of an ammonium glycolate solution (concentration of ammonium glycolate: 15.8 weight %), and then the water-splitting electrodialysis with a double-chambered water-splitting electrodialysis device described in Example 5 was performed to obtain 1.5 kg of a glycolic acid solution (concentration of glycolic acid: 12.2 weight %). Furthermore, the concentration treatment described in Example 7 was performed, whereby 226 g of a 80 weight % glycolic acid solution was obtained and subsequently the glycolic acid solution was subjected to the cooling crystallization described in Example 8 to obtain 131 g of glycolic acid. 280 ppm of ammonium ion remained in the obtained glycolic acid. Using the glycolic acid as a raw material, a polycondensation reaction was carried out to prepare polyglycolic acid. The polymerization procedure was conducted in the following manner.

First Step

To a 4-necked flask equipped with a stirring device, a thermometer, a dewatering conduit and a cock without bottom 100.0 g of the foregoing aqueous glycolic acid solution adjusted to 70 weight % with distilled water was introduced. After repeating degassing and nitrogen substitution 3 times while stirring, the resulting material was heated in an ordinary pressure from room temperature to 140 degree centigrade for 2 hours for roughly dehydrating moisture contained in the aqueous glycolic acid solution. Thereafter, by maturing in an ordinary pressure at 140 degree centigrade for 1 hour and subsequently decompressing from ordinary pressure to 70 kPa at 140 degree centigrade little by little, remained moisture and condensed water were removed. In this stage, the viscosity of the solution in the flask was a little increased. Furthermore, the solution was matured at 70 kPa, at 140 degree centigrade for 30 minutes, and then returned to ordinary pressure, and the content was taken out from the cock without bottom of the reaction flask. By taking the content out and rapidly cooling it, the content became an oligomer of a white crystal solid. The yield of the obtained white crystal solid oligomer was 50.9 g. In this stage, the molecular weight of the polyglycolic acid oligomer was 6,000 in terms of the weight average molecular weight (Mw).

Second Step

The above obtained polyglycolic acid oligomer solid was pulverized and classified to give a pellet having a particle diameter of 2.36 to 1.00 mm. 20 g of this pellet was filled in a SUS column having an inner volume of 100 cc capable of nitrogen circulation. This column was fixed in an inert oven, and the resulting material was subjected to a solid polymerization step by step at each temperature of 120, 180, 200, 210 and 220 degree centigrade for 20 hours respectively under the condition of a nitrogen gas flow rate, that is, a specific velocity (hereinafter referred to as Sv) of 200 ml/hr/g. After the last solid polymerization at 220 degree centigrade, a pellet of the polyglycolic acid was recovered. To evaluate the quality of the obtained polyglycolic acid, the color and the molecular weight were evaluated. For the color, 1.9 g of 1N sodium hydroxide was added to 0.1 g of the obtained polyglycolic acid, and the resulting solution was incubated in a thermostatic bath at 50 degree centigrade for 20 hours, hydrolyzed and then diluted with 3.0 g of distilled water to give a sample. The transmittance of the sample was measured at 300 nm using a UV/Vis absorption spectrophotometer. 3 mg of the obtained polyglycolic acid was heated using an oven at 250 degree centigrade for 2 minutes to obtain an amorphous polymer and the resulting amorphous polymer was dissolved in hexafluoroisopropanol for measuring the molecular weight using GPC. The results were shown in Table 2.

TABLE 2

| Color (Transmittance %) | Molecular weight (Mw) |
|---|---|
| 68.1 | 87000 |

Example 10

Polymerization Evaluation of Glycolic Acid Produced by Combining Activated Carbon Treatment with a Double-Chambered Electrodialysis Device, Concentration Treatment and Cooling Crystallization Using the *Escherichia coli* MG1655/pGAPfucO-aldA strain described in Example 1, 2 kg of the ammonium glycolate solution (concentration of ammonium glycolate: 12.9 weight %) obtained by the method as described in Example 2 was subjected to the activated carbon treatment described in Example 4 to obtain 2 kg of ammonium glycolate (concentration of ammonium glycolate: 12.8 weight %). Subsequently, the treatment with double-chambered water-splitting electrodialysis device described in Example 5 was conducted to obtain 1.4 kg of a glycolic acid solution (concentration of glycolic acid: 13.0 weight %). Thereafter, the concentration treatment described in Example 7 was performed, whereby 230 g of a 80 weight % glycolic acid solution was obtained, and then the glycolic acid solution was subjected to the cooling crystallization described in Example 8 to obtain 133 g of glycolic acid. In the obtained glycolic acid, the concentration of ammonium ion was 300 ppm. Using the glycolic acid as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 3.

TABLE 3

| Color (Transmittance %) | Molecular weight (Mw) |
|---|---|
| 63.0 | 89000 |

Example 11

Polymerization Evaluation of Glycolic Acid Produced by Combining Treatment with the Double-Chambered Electrodialysis Device, Treatment with Cation Exchange Resin, Concentration Treatment and Cooling Crystallization Using the *Escherichia coli* MG1655/pGAPfucO-aldA strain described in Example 1, 2 kg of the ammonium glycolate solution (concentration of ammonium glycolate: 12.9 weight %) obtained by the method as described in Example 2 was subjected to the double-chamber anion/cation exchange membrane electrodialysis described in Example 3 to obtain 1.5 kg of an ammonium glycolate solution (concentration of ammonium glycolate: 16.8 weight %). Subsequently, the double-chamber water-splitting electrodialysis described in Example 5 was conducted to obtain 1.4 kg of a glycolic acid solution (concentration of glycolic acid: 13.0 weight %), and then the cation exchange resin treatment described in Example 6 was performed to obtain 1.5 kg of a glycolic acid solution (concentration of glycolic acid: 12.3 weight %). Furthermore, the concentration treatment described in Example 7 was performed, whereby 230 g of a 80 weight % glycolic acid solution was obtained, and subsequently the glycolic acid solution was subjected to the cooling crystallization described in Example 8 to obtain 133 g of glycolic acid. In the obtained glycolic acid, the concentration of ammonium ion was less than the limit of detection (1 ppm). Using the glycolic acid as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 4.

TABLE 4

| Color (Transmittance %) | Molecular weight (Mw) |
|---|---|
| 90.4 | 92000 |

Example 12

Polymerization Evaluation of Glycolic Acid Produced by Combining Treatment with the Double-Chambered Electrodialysis Device Comprised the Anion Exchange Membrane and the Cation Exchange Membrane, Concentration Treatment and Cooling Crystallization Using the *Escherichia coli* MG1655/pGAPfucO-aldA strain described in Example 1, 2 kg of the ammonium glycolate solution (concentration of ammonium glycolate: 12.9 weight %) obtained by the method as described in Example 2 was subjected to the electrodialyzing with a double-chambered electrodialysis device comprised the anion exchange membrane and the cation exchange membrane described in Example 3 to obtain 1.5 kg of an ammonium glycolate solution (concentration of ammonium glycolate: 16.8 weight %). Then, the water-splitting electrodialysis with a double-chambered water-splitting electrodialysis device described in Example 5 was conducted to obtain 1.4 kg of a glycolic acid solution (concentration of glycolic acid: 13.0 weight %), and then the concentration treatment described in Example 7 was performed to obtain 230 g of a 80 weight % glycolic acid solution. Subsequently, the glycolic acid solution was subjected to the cooling crystallization described in Example 8, and the obtained crystals were washed with 130 g of the 80 weight % glycolic acid solution separately prepared 5 times to obtain 110 g of glycolic acid. 1 ppm of ammonium ion remained in the obtained glycolic acid. Further, when the crystals were washed with 80 weight % glycolic acid 3 times, 120 g of glycolic acid was obtained. 5 ppm of ammonium ion remained in the obtained glycolic acid. Furthermore, when the crystals were not washed with 80 weight % glycolic acid, 130 g of the glycolic acid was recovered and 380 ppm of ammonium ion remained therein. Using the glycolic acid as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 5.

TABLE 5

| Washing procedure | Ammonium ion (ppm) | Color (Transmittance %) | Molecular weight (Mw) |
|---|---|---|---|
| Yes (5 times) | 1 | 88.0 | 72000 |
| Yes (3 times) | 5 | 80.0 | 72000 |
| No | 380 | 61.0 | 72000 |

Example 13

Polymerization Evaluation of Glycolic Acid Produced by Combining Double-Chamber Electrodialysis with Activated Carbon treatment, cation exchange resin treatment, Concentration Treatment and Cooling Crystallization Using the *Escherichia coli* MG1655/pGAPfucO-aldA strain described in Example 1, 2 kg (concentration of ammonium glycolate: 12.9 weight %) of the ammonium glycolate solution obtained by the method as described in Example 2 was subjected to the double-chamber anion/cation exchange membrane electrodialysis described in Example 3 to obtain 1.5 kg of an ammonium glycolate solution (concentration of ammonium glycolate: 16.8 weight %). Subsequently, the activated carbon treatment described in Example 4 was conducted to obtain 1.6 kg of an ammonium glycolate solution (concentration of ammonium glycolate: 15.8 weight %), and then the double-chamber water-splitting electrodialysis described in Example 5 was performed to obtain 1.5 kg of a glycolic acid solution (concentration of glycolic acid: 12.2 weight %). Furthermore, the cation exchange resin treatment described in Example 6 was performed, whereby 1.6 kg of a glycolic acid solution (concentration of glycolic acid: 11.4 weight %) was obtained, while the concentration treatment described in Example 7 was performed, whereby 226 g of a 80 weight % glycolic acid solution was obtained. Next, the glycolic acid solution was subjected to the cooling crystallization described in Example 8 to obtain 131 g of glycolic acid. In the obtained glycolic acid, the concentration of ammonium ion was less than the limit of detection (1 ppm). Using the glycolic acid as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 6.

TABLE 6

| Color (Transmittance %) | Molecular weight (Mw) |
|---|---|
| 88.8 | 83000 |

Example 14

Polymerization Evaluation of Glycolic Acid Produced by Combining Activated Carbon Treatment with the Double-Chambered Electrodialysis Device, Treatment with the Cation Exchange Resin, Concentration Treatment and Cooling Crystallization Using the *Escherichia coli* MG1655/pGAPfucO-aldA strain described in Example 1, 2 kg of an ammonium glycolate solution (concentration of ammonium glycolate: 12.9 weight %) obtained by the method as described in Example 2 was subjected to the activated carbon treatment described in Example 4 to obtain 2 kg of an ammonium glycolate solution (concentration of ammonium glycolate: 12.8 weight %). Subsequently, the water-splitting electrodialysis with a double-chambered water-splitting electrodialysis device described in Example 5 was conducted to obtain 1.5 kg of a glycolic acid solution (concentration of glycolic acid: 12.2 weight %). The cation exchange resin treatment described in Example 6 was performed to obtain 1.6 kg of a glycolic acid solution (concentration of glycolic acid: 11.4 weight %), while the concentration treatment described in Example 7 was performed to obtain 226 g of a 80 weight % glycolic acid solution. Next, the glycolic acid solution was subjected to the cooling crystallization described in Example 8 to obtain 131 g of glycolic acid. In the obtained glycolic acid, the concentration of ammonium ion was less than the limit of detection (1 ppm). Using the glycolic acid as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 7.

TABLE 7

| Color (Transmittance %) | Molecular weight (Mw) |
|---|---|
| 90.0 | 84000 |

Example 15

Polymerization Evaluation of Glycolic Acid Obtained by Purifying a Glycolate Solution in which 10 Mole % of Ethylene Glycol Based on Glycolate Remained Using the *Escherichia coli* MG1655/pGAPfucO-aldA strain described in Example 1, an ammonium glycolate solution (concentration of ammonium glycolate: 11.6 weight %) was obtained by the method as described in Example 2 by changing an aeration rate to 0.2 vvm and an agitation rate to 500 rpm. 10 mole % of ethylene glycol based on ammonium glycolate remained in this solution. 2 kg of the ammonium glycolate solution was subjected to the electrodialysis with a double-chambered electrodialysis device comprised the anion exchange membrane and the cation exchange membrane described in Example 3 to obtain 1.5 kg of an ammonium glycolate solution (concentration of ammonium glycolate: 15.0 weight %, concentration of ethylene glycol: 1.0 mole % based on ammonium glycolate). Subsequently, the water-splitting electrodialysis with a double-chambered water-splitting electrodialysis device described in Example 5 was conducted to obtain 1.4 kg of a glycolic acid solution (concentration of glycolic acid: 11.6 weight %, concentration of ethylene glycol: 1.15 mole % based on glycolic acid), and then the cation exchange resin treatment described in Example 6 was performed to obtain 1.5 kg of a glycolic acid solution (concentration of glycolic acid: 11.0 weight %, concentration of ethylene glycol: 1.15 mole % based on glycolic acid). Furthermore, the concentration treatment described in Example 7 was performed, whereby 207 g of a 80 weight % glycolic acid solution (concentration of ethylene glycol: 1.15 mole % based on glycolic acid) was obtained. Subsequently, the glycolic acid solution was subjected to the cooling crystallization described in Example 8 to obtain 120 g of glycolic acid (concentration of ethylene glycol: 0.16 mole % based on glycolic acid). In the obtained glycolic acid, the concentration of ammonium ion was less than the limit of detection (1 ppm). Using the glycolic acid as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 8.

TABLE 8

| Color (Transmittance %) | Molecular weight (Mw) |
|---|---|
| 89.2 | 20000 |

Figure 4:
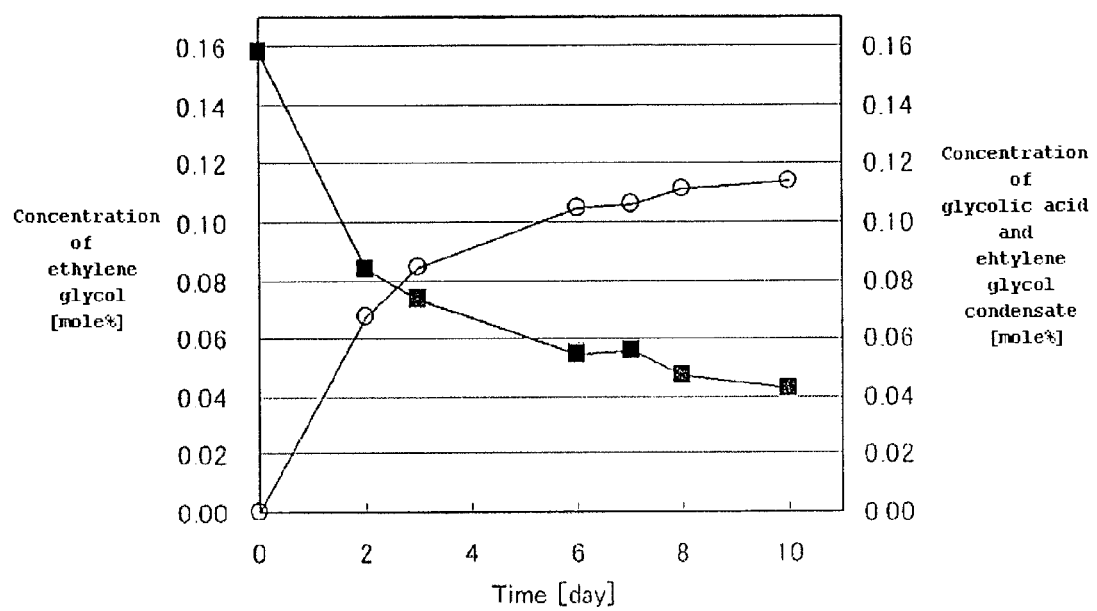
FIG. 4 is a view illustrating the increase of a condensate of glycolic acid and ethylene glycol, and the decrease of ethylene glycol with time when 0.16 mole % of ethylene glycol remains in the glycolic acid in Example 15.

In Example 15, to produce polyglycolic acid, there was no problem in the color, but since the remaining concentration of ethylene glycol was high, it was obvious that the molecular weight was lowered. Accordingly, it was shown that the concentration of ethylene glycol was preferably less than 0.1% as a molar ratio based on the purified glycolic acid. Furthermore, the compositional changes when the glycolic acid was kept at 25 degree centigrade for 10 days were observed with time and the results thereof were shown in FIG. 4. As shown in FIG. 4, when 0.16 mole % of ethylene glycol based on the glycolic acid remained in the glycolic acid, it was shown that the glycolic acid and ethylene glycol were spontaneously reacted with each other so that the condensate thereof was increased with time. Further, when the polymerization evaluation was performed using this as a raw material, it was obvious that polyglycolic acid having a small molecular weight was obtained as shown in the results of Table 8. Incidentally, in FIG. 4, a black square indicates the concentration (mole %) of ethylene glycol, while a circle indicates the concentration of the condensate of glycolic acid and ethylene glycol.

Example 16

Polymerization Evaluation of Glycolic Acid Obtained by Purifying the Glycolate Solution in which 4.9 Mole % of Ethylene Glycol Based on Glycolate Remained Using the *Escherichia coli* MG1655/pGAPfucO-aldA strain described in Example 1, an ammonium glycolate solution (concentration of ammonium glycolate: 12.3 weight %) was obtained by the method as described in Example 2 by changing an aeration rate to 0.5 vvm and an agitation rate to 600 rpm. 4.9 mole % of ethylene glycol based on ammonium glycolate remained in this solution. 2 kg of the ammonium glycolate solution was subjected to the electrodialysis with a double-chambered electrodialysis device comprised the anion exchange membrane and the cation exchange membrane described in Example 3 to obtain 1.5 kg of an ammonium glycolate solution (concentration of ammonium glycolate: 15.9 weight %, concentration of ethylene glycol: 0.49 mole % based on ammonium glycolate). Subsequently, the water-splitting electrodialysis with a double-chambered water-splitting electrodialysis device described in Example 5 was conducted to obtain 1.4 kg of a glycolic acid solution (concentration of glycolic acid: 12.3 weight %, concentration of ethylene glycol: 0.55 mole % based on glycolic acid), and then the cation exchange resin treatment described in Example 6 was performed to obtain 1.5 kg of a glycolic acid solution (concentration of glycolic acid: 11.6 weight %, concentration of ethylene glycol: 0.55 mole % based on glycolic acid). Furthermore, the concentration treatment described in Example 7 was performed, whereby 219 g of a 80 weight % glycolic acid solution (concentration of ethylene glycol: 0.55 mole % based on glycolic acid) was obtained. Subsequently, the glycolic acid solution was subjected to the cooling crystallization described in Example 8 to obtain 127 g of glycolic acid (concentration of ethylene glycol: 0.076 mole % based on glycolic acid). In the obtained glycolic acid, the concentration of ammonium ion was less than the limit of detection (1 ppm). Using the glycolic acid as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 9.

TABLE 9

| Color (Transmittance %) | Molecular weight (Mw) |
| --- | --- |
| 89.2 | 71000 |

Example 17

Polymerization Evaluation of Glycolic Acid Obtained by Purifying the Glycolate Solution in which 1.0 Mole % of Ethylene Glycol Based on Glycolate Remained Using the *Escherichia coli* MG1655/pGAPfucO-aldA strain described in Example 1, an ammonium glycolate solution (concentration of ammonium glycolate: 12.7 weight %) was obtained by the method as described in Example 2 by changing an aeration rate to 0.8 vvm and an agitation rate to 700 rpm. 1.0 mole % of ethylene glycol based on ammonium glycolate remained in this solution. 2 kg of the ammonium glycolate solution was subjected to the electrodialysis with a double-chambered electrodialysis device comprised the anion exchange membrane and the cation exchange membrane described in Example 3 to obtain 1.5 kg of an ammonium glycolate solution (concentration of ammonium glycolate: 16.5 weight %, concentration of ethylene glycol: 0.1 mole % based on ammonium glycolate). Subsequently, the water-splitting electrodialysis with a double-chambered water-splitting electrodialysis device described in Example 5 was conducted to obtain 1.4 kg of a glycolic acid solution (concentration of glycolic acid: 12.7 weight %, concentration of ethylene glycol: 0.11 mole % based on glycolic acid), and then the cation exchange resin treatment described in Example 6 was performed to obtain 1.5 kg of a glycolic acid solution (concentration of glycolic acid: 12.0 weight %, concentration of ethylene glycol: 0.55 mole % based on glycolic acid). Furthermore, the concentration treatment described in Example 7 was performed, whereby 226 g of a 80 weight % glycolic acid solution (concentration of ethylene glycol: 0.11 mole % based on glycolic acid) was obtained. Subsequently, the glycolic acid solution was subjected to the cooling crystallization described in Example 8 to obtain 131 g of glycolic acid (concentration of ethylene glycol: 0.015 mole % based on glycolic acid). In the obtained glycolic acid, the concentration of ammonium ion was less than the limit of detection (1 ppm). Using the glycolic acid as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 10.

TABLE 10

| Color (Transmittance %) | Molecular weight (Mw) |
| --- | --- |
| 90.2 | 90000 |

Example 18

Polymerization Evaluation of Glycolic Acid Produced by Combining Activated Carbon Treatment, Electrodialysis with a Double-Chambered Electrodialysis Device, Cation Exchange Resin Treatment and Activated Carbon Treatment Using the *Escherichia coli* MG1655/pGAPfucO-aldA strain described in Example 1, 2 kg of an ammonium glycolate solution (concentration of ammonium glycolate: 12.9 weight %) obtained by the method as described in Example 2 was subjected to the activated carbon treatment described in Example 4 to obtain 2 kg of an ammonium glycolate solution (concentration of ammonium glycolate: 12.8 weight %). Subsequently, the water-splitting electrodialysis with a double-chambered water-splitting electrodialysis device described in Example 5 was conducted to obtain 1.5 kg of a glycolic acid solution (concentration of glycolic acid: 12.2 weight %). The cation exchange resin treatment described in Example 6 was performed to obtain 1.6 kg of a glycolic acid solution (concentration of glycolic acid: 11.4 weight %). Furthermore, the activated carbon treatment described in Example 4 was performed, whereby 1.6 g of a glycolic acid solution (concentration of glycolic acid: 11.3 weight %) was obtained. Using the glycolic acid as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 11.

TABLE 11

| Color (Transmittance %) | Molecular weight (Mw) |
|---|---|
| 89.9 | 89000 |

Example 19

Polymerization Evaluation of Glycolic Acid Produced by Combining Activated Carbon Treatment, Electrodialysis with a Double-Chambered Electrodialysis Device, Activated Carbon Treatment and Cation Exchange Resin Treatment Using the *Escherichia coli* MG1655/pGAPfucO-aldA strain described in Example 1, 2 kg of an ammonium glycolate solution (concentration of ammonium glycolate: 12.9 weight %) obtained by the method as described in Example 2 was subjected to the activated carbon treatment described in Example 4 to obtain 2 kg of an ammonium glycolate solution (concentration of ammonium glycolate: 12.8 weight %). Subsequently, the water-splitting electrodialysis with a double-chambered water-splitting electrodialysis device described in Example 5 was conducted to obtain 1.5 kg of a glycolic acid solution (concentration of glycolic acid: 12.2 weight %). Furthermore, the activated carbon treatment described in Example 4 was performed, whereby 1.5 kg of a glycolic acid solution (concentration of glycolic acid: 12.1 weight %) was obtained. The cation exchange resin treatment described in Example 6 was performed to obtain 1.5 kg of a glycolic acid solution (concentration of glycolic acid: 12.1 weight %). Using the glycolic acid as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 12.

TABLE 12

| Color (Transmittance %) | Molecular weight (Mw) |
|---|---|
| 90.0 | 90000 |

Comparative Example 1

Polymerization Evaluation Using Glycolic Acid of a Commercial/Industrial Class as a Raw Material Using glycolic acid (a product of Wako Pure Chemical Industries, Ltd.) of a commercial/industrial class produced in according with U.S. Pat. No. 3,859,349 as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 13.

TABLE 13

| Color (Transmittance %) | Molecular weight (Mw) |
|---|---|
| 20.7 | 49000 |

As shown in Table 13, when glycolic acid of a commercial/industrial class was used, the transmittance was low, that is, polyglycolic acid with a high color was obtained as compared to the case where the glycolic acid obtained by the production process illustrated in the present invention was used.

Comparative Example 2

Polymerization Evaluation Using Commercial Glycolic Acid Having a High Purity as a Raw Material Using commercial glycolic acid (a product of Tokyo Kasei Kogyo Co., Ltd.) having a high purity produced in according with Japanese Patent Laid-open No. 1994-501268 as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 14.

TABLE 14

| Color (Transmittance %) | Molecular weight (Mw) |
|---|---|
| 52.1 | 71000 |

As shown in Table 14, even when commercial glycolic acid having a high purity was used, the transmittance was low, that is, polyglycolic acid with a high color was obtained as compared to the case where the glycolic acid obtained by the production process illustrated in the present invention was used.

Comparative Example 3

Polymerization Evaluation of Glycolic Acid Obtained by Electrodialysis and Concentration Treatment Using the *Escherichia coli* MG1655/pGAPfucO-aldA strain described in Example 1, 2 kg of an ammonium glycolate solution (concentration of ammonium glycolate: 12.9 weight %) obtained by the method as described in Example 2 was subjected to the electrodialysis with a double-chambered electrodialysis device comprised the anion exchange membrane and the cation exchange membrane described in Example 3 to obtain 1.5 kg of an ammonium glycolate solution (concentration of ammonium glycolate: 16.8 weight %). Subsequently, the water-splitting electrodialysis with a double-chambered water-splitting electrodialysis device described in Example 5 was conducted to obtain 1.4 kg of a glycolic acid solution (concentration of glycolic acid: 13.0 weight %), and then the concentration treatment described in Example 7 was performed to obtain 231 g of a 80 weight % glycolic acid solution. 4,900 ppm of ammonium ion remained in the obtained glycolic acid. Using the glycolic acid as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 15.

TABLE 15

| Color (Transmittance %) | Molecular weight (Mw) |
|---|---|
| 26.8 | 72000 |

As shown in Table 15, when glycolic acid was purified only by the electrodialysis and concentration treatment, ammonium ion remained in high concentration. As shown in Examples 9 to 19, the transmittance was low, that is, polyglycolic acid with a high color was obtained as compared to the case where the activated carbon treatment was combined with the cation exchange resin treatment and the cooling crystallization for purification.

Example 20

Production of Glycolic Acid Using the Glycolic Acid Solution Produced by Using Glycolonitrile as a Raw Material and Polymerization Evaluation Using the Same as a Raw Material Using the method as described in Example 1 of International Publication No. WO 2002/068658, an ammonium glycolate solution was produced. Specifically, it was produced in the following manner. 938 mL of 0.1M potassium phosphate solution (pH: 7.0) in which 62 g of *Acidovorax facilis* 72W (ATCC55746) with wet fungus body was suspended was heated at 50 degree centigrade for 1 hour for deactivation of nitrile hydratase activity and amidase activity, and then cooled using a water bath at 25 degree centigrade. The resulting material was subjected to the centrifugation for removing a supernatant, and then re-dispersed in 948 mL of 0.02M potassium phosphate solution (pH: 6.0) and further subjected to the centrifugation for removing the supernatant. The obtained fungus body was re-dispersed in 938 mL of 0.02M potassium phosphate solution (pH: 6.0) and 106 mL of an aqueous solution of 55 weight % glycolonitrile was added thereto, and the resulting mixture was stirred at 25 degree centigrade for 2 hours. After stirring, the solution was subjected to the centrifugation for recovering the supernatant. According to the procedure, the added glycolonitrile was completely changed to ammonium glycolate. The above procedure was repeated several times and 3.3 kg of the obtained ammonium glycolate solution (concentration of ammonium glycolate: 8.4 weight %) was subjected to the electrodialysis with a double-chambered electrodialysis device comprised the anion exchange membrane and the cation exchange membrane described in Example 3 to obtain 2.5 kg of an ammonium glycolate solution (concentration of ammonium glycolate: 10.8 weight %). Subsequently, the activated carbon treatment described in Example 4 was performed to obtain 2.6 kg of an ammonium glycolate solution (concentration of ammonium glycolate: 10.2 weight %), and then the water-splitting electrodialysis with a double-chambered water-splitting electrodialysis device described in Example 5 was performed to obtain 2.5 kg of a glycolic acid solution (concentration of glycolic acid: 7.9 weight %). The cation exchange resin treatment described in Example 6 was performed to obtain 2.6 kg of a glycolic acid solution (concentration of glycolic acid: 7.5 weight %), and the concentration treatment described in Example 7 was further performed to obtain 243 g of a 80 weight % glycolic acid solution. Next, the glycolic acid solution was subjected to the cooling crystallization described in Example 8 to obtain 141 g of glycolic acid. In the obtained glycolic acid, the concentration of ammonium ion was less than the limit of detection (1 ppm). Using the glycolic acid as a raw material, a polycondensation reaction was conducted to produce polyglycolic acid. The evaluation of the color and evaluation of the molecular weight of the polyglycolic acid obtained by the polymerization procedure and polymerization were conducted in the same manner as in Example 9. The results were shown in Table 16. Incidentally, the aforementioned ATCC number refers to a deposit number in the Amerimay Type Culture Collection, while the aforementioned strain is requested to the Amerimay Type Culture Collection so that it is available to any person upon payment.

TABLE 16

| Color (Transmittance %) | Molecular weight (Mw) |
|---|---|
| 89.2 | 95000 |

As shown in Table 16, the purification method according to the present invention was suitable even to an ammonium glycolate solution obtained by using glycolonitrile as a raw material, while the polyglycolic acid obtained by the polymerization of the obtained glycolic acid exhibited that coloring was small and the molecular weight was great.

Example 21

Polymerization Evaluation of Glycolic Acid by Producing a Glycolic Acid Copolymer Using the glycolic acid obtained in Example 17, a glycolic acid copolymer was produced. Specifically, 100 weight parts of glycolic acid, 29.7 weight parts of isophthalic acid, 38.9 weight parts of ethylene glycol and 0.08 weight parts of trimethylolethane were introduced to a reaction bath. The resulting material was subjected to an esterification reaction for about 24 hours while removing water generated in an ordinary pressure of nitrogen atmosphere, under stirring at 130 to 200 degree centigrade until it became transparent. The obtained polyester oligomer was introduced to a glass reactor equipped with a stirring device and an outflow tube. The outflow tube was connected to a vacuum device consisting of a vacuum pump and a vacuum regulator, forming a structure such that an evaporant could be removed. 0.6 weight parts of a germanium catalyst (6.7 weight % of germanium dioxide contained) were added thereto. First, the resulting mixture was reacted in a nitrogen flow under stirring at 200 degree centigrade for 30 minutes. Thereafter, the reactor was maintained at 200 degree centigrade and decompressed down to near 0.8 torr for about 1 hour, and then the reaction was performed by heating up to 225 degree centigrade while stirring under the condition of about 0.8 to 0.5 torr for about 10 hours for removing generated ethylene glycol from the reactor. Compositions of respective component units of glycolic acid, isophthalic acid, ethylene glycol and diethylene glycol in the polycondensate were respectively 71.0 mole %, 14.5 mole %, 10.1 mole % and 4.4 mole %. The polyester resin was dried under reduced pressure at about 40 degree centigrade for about 20 hours, and then interposed between two brass plates, aluminum plates and mold release films in a predetermined amount. The resulting material was melted at 200 degree centigrade, compressed at 10 MPa for 1 minute, and then compressed again at 10 MPa using a compression molding machine set at a temperature of 20 degree centigrade for cooling to prepare a press film having a thickness of about 70 μm. The obtained film was transparent and the Δb value was 6.7%.

Comparative Example 4

Polymerization Evaluation of Glycolic Acid by Producing a Glycolic Acid Copolymer Using Commercial Glycolic Acid Having a High Purity as a Raw Material Using glycolic acid (a product of Wako Pure Chemical Industries, Ltd.) of a commercial/industrial class produced in according with U.S. Pat. No. 3,859,349 as a raw material, a polycondensation reaction was conducted to produce a glycolic acid copolymer. The evaluation of the color of the polyglycolic acid obtained by the polymerization procedure and polymerization was conducted in the same manner as in Example 21. As a result, the obtained film was a little colored and the Δb value was 12.8%. Even when the glycolic acid copolymer was produced and the glycolic acid produced by the production process described in the present invention was used, a glycolic acid copolymer having a low color was obtained as compared to the case where a commercial glycolic acid having a high purity was used.

The physical properties of glycolic acids and polyglycolic acids obtained according to Examples 3 to 20 and Comparative Examples 1 to 3 are shown in Table 17, while the physical properties of glycolic acids and glycolic acid copolymers obtained according to Example 21 and Comparative Example 4 are shown in Table 18 below. Incidentally, the concentration of the glycolic acid in each glycolic acid, the molar ratio of ethylene glycol and concentration of ammonium ion are values obtained when moisture is removed.

TABLE 17

| Production No. | | Order of steps | | | | | | Glycolic acid Concentration of glycolic acid (wt %) | Molar ratio of ethylene glycol (%)* | Glycolic acid Concentration of ammonium ion (ppm)* | Polyglycolic acid Color (transmittance: %) | Polyglycolic acid Molecular weight (Mw) |
|---|---|---|---|---|---|---|---|---|---|---|---|---|
| 1 | Examples 3 to 8 | a1 | c | a2 | d | e | b | 99.99 | 0.010 | less than 1 ppm | — | — |
| 2 | Example 9 | a1 | c | a2 | e | b | | 99.99 | 0.012 | 280 | 68.1 | 87000 |
| 3 | Example 10 | c | a2 | e | b | | | 99.99 | 0.012 | 300 | 63.0 | 89000 |
| 4 | Example 11 | a1 | a2 | d | e | b | | 99.99 | 0.010 | less than 1 ppm | 90.4 | 92000 |
| 5 | Example 12 | a1 | a2 | e | b | | | 99.94 | 0.075 | 1 | 88.0 | 72000 |
| | | | | | | | | | | 5 | 80.0 | 72000 |
| | | | | | | | | | | 380 | 61.0 | 72000 |
| 6 | Example 13 | a1 | c | a2 | d | e | b | 99.99 | 0.012 | less than 1 ppm | 88.8 | 83000 |
| 7 | Example 14 | c | a2 | d | e | b | | 99.99 | 0.011 | less than 1 ppm | 90.0 | 84000 |
| 8 | Example 15 | a1 | a2 | d | e | b | | 99.87 | 0.160 | less than 1 ppm | 89.2 | 20000 |
| 9 | Example 16 | a1 | a2 | d | e | b | | 99.94 | 0.076 | less than 1 ppm | 89.2 | 71000 |
| 10 | Example 17 | a1 | a2 | d | e | b | | 99.99 | 0.015 | less than 1 ppm | 90.2 | 90000 |
| 11 | Example 18 | c | a2 | d | c | | | 99.99 | 0.012 | less than 1 ppm | 89.9 | 89000 |
| 12 | Example 19 | c | a2 | c | d | | | 99.99 | 0.013 | less than 1 ppm | 90.0 | 90000 |
| 13 | Comparative Example 1 | Commercial products used | | | | | | 82.00 | — | — | 20.7 | 49000 |
| 14 | Comparative Example 2 | Commercial products used | | | | | | 99.90 | — | — | 52.1 | 71000 |
| 15 | Comparative Example 3 | a1 | a2 | e | | | | 98.14 | 0.075 | 4900 | 26.8 | 72000 |
| 16 | Example 20 | a1 | c | a2 | d | e | b | 99.99 | 0.007 | less than 1 ppm | 89.2 | 95000 |

*Value based on the glycolic acid

TABLE 18

| Production No. | | Order of steps | | | | | Concentration of glycolic acid (wt %) | Glycolic acid Molar ratio of ethylene glycol (%)* | Concentration of ammonium ion (ppm)* | Glycolic acid copolymer Color (Δb: %) |
|---|---|---|---|---|---|---|---|---|---|---|
| 17 | Example 21 | a1 | a2 | d | e | b | 99.99 | 0.010 | less than 1 ppm | 6.7 |
| 18 | Comparative Example 4 | Commercial products used | | | | | 99.99 | — | — | 12.8 |

*Value based on the glycolic acid

---

The invention claimed is:

1. A process for producing polyglycolic acid comprising:
producing glycolic acid from glycolate and
producing polyglycolic acid from the glycolic acid as a raw material by a polymerization method,
wherein the process for producing glycolic acid from glycolate comprises:
a first step for carrying out the following step(s) (a1) and/or (c) for a solution containing glycolate;
a second step for carrying out the following step (a2) after said first step to transform the glycolate into glycolic acid; and
a third step for carrying out the following step(s) (b) and/or (d) after said second step,
(a1) step for electrodialyzing with an anion exchange membrane and a cation exchange membrane;
(a2) step for water-splitting electrodialysis;
(b) step for cooling crystallization;
(c) step for treatment with an activated carbon; and
(d) step for treatment with a cation exchange resin, and
wherein said polymerization method includes:
producing a oligomer by dehydrating the glycolic acid;
carrying out solid polymerization of the oligomer.

2. The process for producing polyglycolic acid as set forth in claim 1, wherein
the step (a1) is a step for obtaining a glycolate solution by supplying the solution containing glycolate to a desalination chamber of an electrodialysis device having desalination chambers and concentrating chambers formed by alternately arranging anion exchange membranes and cation exchange membranes between electrodes for conducting electrodialysis, and transmitting a glycolic acid anion and a monovalent cation from said ion exchange membrane; and
the step (a2) is a step for obtaining the glycolic acid solution by supplying the glycolate solution after said first step as it is or via an optional step to the acid chamber of a water-splitting electrodialysis device having acid chambers and base chambers formed by alternately arranging a bipolar membrane and a cation exchange membrane, and acidifying the glycolic acid anion by electrolysis of water through the bipolar membrane.

3. The process for producing polyglycolic acid as set forth in claim 1, further comprising a step for producing the solution containing the glycolate by oxidizing an ethylene glycol before said first step.

4. The process for producing polyglycolic acid set forth in claim 3, wherein the solution containing glycolate is obtained by bringing a microorganism having the ability to produce glycolic acid by oxidizing ethylene glycol into contact with the ethylene glycol in the presence of oxygen, in said step for producing the solution containing glycolate.

5. The process for producing polyglycolic acid as set forth in claim 4, wherein said microorganism belongs to the genus *Escherichia*.

6. The process for producing polyglycolic acid as set forth in claim 1, wherein the solution containing glycolate in which the molar ratio of the ethylene glycol to a purified glycolic acid is less than 0.1% is obtained after said third step.

7. The process for producing polyglycolic acid as set forth in claim 1, wherein the solution containing glycolate in which the concentration of the ethylene glycol in the solution containing glycolate is less than 5% as a molar ratio based on the glycolate is used in said first step.

8. The process for producing polyglycolic acid as set forth in claim 1, wherein the glycolic acid with the total concentration of the counter cation to the glycolic acid other than hydrogen ion of from 0 to 5 ppm is obtained after said third step.

9. The process for producing polyglycolic acid as set forth in claim 1, wherein the step (a1) is a step for electrodialyzing with a double-chambered electrodialysis device comprised an anion exchange membrane and a cation exchange membrane, and the step (a2) is a step for water-splitting electrodialysis with a double-chambered water-splitting electrodialysis device.

10. A process for producing polyglycolic acid comprising:
producing glycolic acid from ammonium glycolate; and
producing polyglycolic acid from the glycolic acid as a raw material by a polymerization method,
wherein the process for producing glycolic acid from ammonium glycolate comprises:
a first step for carrying out the following step(s) (a1) and/or (c) for a solution containing ammonium glycolate;
a second step for carrying out the following step (a2) after said first step to transform the ammonium glycolate into glycolic acid; and
a third step for carrying out the following step(s) (b) and/or (d) after said second step,
(a1) step for electrodialyzing with an anion exchange membrane and a cation exchange membrane
(a2) step for water-splitting electrodialysis;
(b) step for cooling crystallization;
(c) step for treatment with an activated carbon; and
(d) step for treatment with a cation exchange resin,
wherein the concentration of ammonium ion in the obtained glycolic acid after said third step is not more than 5 ppm based on the glycolic acid.

11. The process for producing the polyglycolic acid as set forth in claim 10, wherein said polymerization method includes ring-opening polymerization or polycondensation of the glycolic acid via cyclic ester.

12. A process for producing a glycolic acid copolymer comprising:
producing glycolic acid from glycolate; and
producing glycolic acid copolymer by polycondensation of the glycolic acid with one or more compound(s) selected from the group of isophthalic acid, ethylene glycol and diethylene glycol as raw materials,
wherein the process for producing glycolic acid from glycolate comprises:
a first step for carrying out the following step(s) (a1) and/or (c) for a solution containing glycolate;
a second step for carrying out the following step (a2) after said first step to transform the glycolate into glycolic acid; and
a third step for carrying out the following step(s) (b) and/or (d) after said second step,
(a1) step for electrodialyzing with an anion exchange membrane and a cation exchange membrane
(a2) step for water-splitting electrodialysis;
(b) step for cooling crystallization;
(c) step for treatment with an activated carbon; and
(d) step for treatment with a cation exchange resin.

13. The process for producing polyglycolic acid as set forth in claim 1, wherein said first step includes using an aqueous solution of ammonium glycolate as the solution containing glycolate; and said second step includes transforming ammonium glycolate into glycolic acid by acidification
wherein the concentration of ammonium ion in the obtained glycolic acid after said third step is not more than 5 ppm based on the glycolic acid.

14. The process for producing polyglycolic acid as set forth in claim 13, further comprising
a step for producing the aqueous solution of the ammonium glycolate by using a microorganism having an ability to produce the glycolic acid by oxidizing ethylene glycol before said first step.

15. The process for producing polyglycolic acid as set forth in claim 14, wherein said microorganism belongs to the genus *Escherichia*.

16. The process for producing polyglycolic acid as set forth in claim 13, wherein the step (a2) is conducted by using the aqueous solution of the ammonium glycolate to acidify the ammonium glycolate.

17. The process for producing polyglycolic acid as set forth in claim 1, wherein the step (b) is carried out one or two or more times in said third step.

18. The process for producing polyglycolic acid as set forth in claim 17, wherein a step (e) for concentration is carried out just before the step (b) in said third step.

19. The process for producing polyglycolic acid as set forth in claim 17 or 18, wherein the step (d) is carried out after the step (b) in said third step.

20. The process for producing polyglycolic acid as set forth in claim 17 or 18, wherein the step (a1) or (c) is carried out in said first step.

21. The process for producing polyglycolic acid as set forth in claim 17 or 18, wherein the step (c) is carried out after the step (a1) in said first step.

22. The process for producing polyglycolic acid as set forth in claim 17 or 18, wherein the step (c) is further carried out before or after the step (d) in said third step, when the step (c) is carried out in said first step.

23. The process for producing polyglycolic acid as set forth in claim 10, wherein
the step (a1) is a step for obtaining an ammonium glycolate solution by supplying the solution containing ammonium glycolate to a desalination chamber of an electrodialysis device having desalination chambers and concentrating chambers formed by alternately arranging anion exchange membranes and cation exchange membranes between electrodes for conducting electrodialysis, and transmitting a glycolic acid anion and a monovalent cation from said ion exchange membrane; and
the step (a2) is a step for obtaining the glycolic acid solution by supplying the ammonium glycolate solution after said first step as it is or via an optional step to the acid chamber of a water-splitting electrodialysis device having acid chambers and base chambers formed by alternately arranging a bipolar membrane and a cation exchange membrane, and acidifying the glycolic acid anion by electrolysis of water through the bipolar membrane.

24. The process for producing polyglycolic acid as set forth in claim 10, further comprising a step for producing the solution containing glycolate by oxidizing an ethylene glycol before said first step.

25. The process for producing polyglycolic acid as set forth in claim 24, wherein the solution containing ammonium glycolate is obtained by bringing a microorganism having the ability to produce glycolic acid by oxidizing ethylene glycol into contact with the ethylene glycol in the presence of oxygen, in said step for producing the solution containing ammonium glycolate.

26. The process for producing polyglycolic acid as set forth in claim 25, wherein said microorganism belongs to the genus *Escherichia*.

27. The process for producing polyglycolic acid as set forth in claim 10, wherein the solution containing ammonium glycolate in which the molar ratio of the ethylene glycol to a purified glycolic acid is less than 0.1% is obtained after said third step.

28. The process for producing polyglycolic acid as set forth in claim 10, wherein the solution containing ammonium glycolate in which the concentration of the ethylene glycol in the solution containing ammonium glycolate is less than 5% as a molar ratio based on the ammonium glycolate is used in said first step.

29. The process for producing polyglycolic acid as set forth in claim 10, wherein the step (a1) is a step for electrodialyzing with a double-chambered electrodialysis device comprised an anion exchange membrane and a cation exchange membrane, and the step (a2) is a step for water-splitting electrodialysis with a double-chambered water-splitting electrodialysis device.

* * * * *

SEQUENCE LISTING

<160> NUMBER OF SEQ ID NOS: 6

<210> SEQ ID NO 1
<211> LENGTH: 45
<212> TYPE: DNA
<213> ORGANISM: Artificial
<220> FEATURE:
<223> OTHER INFORMATION: Primer for PCR

<400> SEQUENCE: 1
gctctagacg gagaaagtct tatgatggct aacagaatga ttctg         45

<210> SEQ ID NO 2
<211> LENGTH: 29
<212> TYPE: DNA
<213> ORGANISM: Artificial
<220> FEATURE:
<223> OTHER INFORMATION: Primer for PCR

<400> SEQUENCE: 2
gtgaagcttg catttaccag gcggtatgg         29

<210> SEQ ID NO 3
<211> LENGTH: 43
<212> TYPE: DNA
<213> ORGANISM: Artificial
<220> FEATURE:
<223> OTHER INFORMATION: Primer for PCR

<400> SEQUENCE: 3
cgaattccgg agaaagtctt atgtcagtac ccgttcaaca tcc         43

<210> SEQ ID NO 4
<211> LENGTH: 29
<212> TYPE: DNA
<213> ORGANISM: Artificial
<220> FEATURE:
<223> OTHER INFORMATION: Primer for PCR

<400> SEQUENCE: 4
gctctagact ctttcactca ttaagactg         29

<210> SEQ ID NO 5
<211> LENGTH: 30
<212> TYPE: DNA
<213> ORGANISM: Artificial
<220> FEATURE:
<223> OTHER INFORMATION: Primer for PCR

<400> SEQUENCE: 5

```
aacgaattct cgcaatgatt gacacgattc                                              30
```

```
<210> SEQ ID NO 6
<211> LENGTH: 32
<212> TYPE: DNA
<213> ORGANISM: Artificial
<220> FEATURE:
<223> OTHER INFORMATION: Primer for PCR

<400> SEQUENCE: 6
acagaattcg ctatttgtta gtgaataaaa gg                                           32
```